US009687626B2

(12) United States Patent
Amirav et al.

(10) Patent No.: US 9,687,626 B2
(45) Date of Patent: Jun. 27, 2017

(54) SWIVEL ADAPTER FOR NEBULIZER

(75) Inventors: Israel Amirav, Rosh Pina (IL); Asaf Halamish, Pardes Hana-Karkur (IL)

(73) Assignee: NOSTRUM TECHNOLOGY LLC, New Brunswick, NJ (US)

(*) Notice: Subject to any disclaimer, the term of this patent is extended or adjusted under 35 U.S.C. 154(b) by 827 days.

(21) Appl. No.: 13/468,683

(22) Filed: May 10, 2012

(65) Prior Publication Data

US 2012/0285452 A1 Nov. 15, 2012

Related U.S. Application Data

(60) Provisional application No. 61/485,036, filed on May 11, 2011.

(51) Int. Cl.

| | |
|---|---|
| ***A61M 16/00*** | (2006.01) |
| ***A61M 16/08*** | (2006.01) |
| *A61M 11/00* | (2006.01) |
| *A61M 16/04* | (2006.01) |
| *A61M 16/06* | (2006.01) |

(52) U.S. Cl.

CPC .... *A61M 16/0816* (2013.01); *A61M 16/0825* (2014.02); *A61M 11/00* (2013.01); *A61M 16/0488* (2013.01); *A61M 16/06* (2013.01)

(58) Field of Classification Search

CPC .... A61M 11/00; A61M 11/001; A61M 11/02; A61M 11/04; A61M 11/041–11/048; A61M 16/06; A61M 16/08; A61M 16/0825

USPC ............ 128/200.26, 200.27, 207.14, 207.15, 128/207.17, 205.22

See application file for complete search history.

(56) References Cited

U.S. PATENT DOCUMENTS

| | | | | |
|---|---|---|---|---|
| 4,566,452 | A | 1/1986 | Farr | |
| 5,579,757 | A | 12/1996 | McMahon | |
| 5,921,239 | A * | 7/1999 | McCall et al. | 128/205.25 |
| 6,692,179 | B2 * | 2/2004 | Bohne et al. | 403/141 |
| 7,721,734 | B2 | 5/2010 | Rustad | |
| 7,934,501 | B2 | 5/2011 | Fu | |
| 7,954,487 | B2 | 6/2011 | Grychowski | |
| RE42,911 | E | 11/2011 | Denyer | |
| 2005/0065567 | A1 * | 3/2005 | Lee et al. | 607/17 |
| 2007/0107723 | A1 | 5/2007 | Berg | |
| 2007/0227536 | A1 * | 10/2007 | Rivera et al. | 128/200.21 |
| 2009/0151716 | A1 | 6/2009 | Abrams | |
| 2010/0293755 | A1 * | 11/2010 | Draper et al. | 16/430 |
| 2012/0017894 | A1 | 1/2012 | Cinquin | |
| 2012/0085343 | A1 | 4/2012 | Cortez | |

FOREIGN PATENT DOCUMENTS

| | | | |
|---|---|---|---|
| WO | 2010/002421 | A1 | 1/2010 |

OTHER PUBLICATIONS

PARI LC (R) Adult Aerosol Mask (Product Brochure).
PARI Baby (TM) Mask Conversion Kit (Product Brochure).
Devilbiss (Product Brochure).

* cited by examiner

*Primary Examiner* — Peter S Vasat
*Assistant Examiner* — Ned T Heffner
(74) *Attorney, Agent, or Firm* — Scully Scott Murphy and Presser

(57) ABSTRACT

An adapter tube is provided with a pivotally flexible swivel joint providing an aerosol-conducting airway for use with an inhalation mask with a nebulizer.

20 Claims, 4 Drawing Sheets

SWIVEL ADAPTER FOR NEBULIZER

CROSS REFERENCE TO RELATED APPLICATION

This application claims priority under 35 U.S.C. §119(e) to U.S. Provisional Patent Application No. 61/485,036, filed May 11, 2011, the contents of which are hereby incorporated by reference.

FIELD OF THE INVENTION

This invention pertains to medical devices for the inhalation of drugs into the lungs.

BACKGROUND

In the field of respiratory devices, nebulizers are important devices used for the inhalation of drugs in the form of an aerosol. A nebulizer employs an apparatus that generates an aerosol or mist from a solution (usually an aqueous solution) or suspension of a drug. The mist may be an aerosolized suspension or an atomized suspension of drug, meaning micro-droplets suspended in air, medical oxygen, or other inhalable gas. The aerosol is conveyed to the mouth and/or nose of a patient and inhaled into the lungs. In some cases, the mist is conveyed to the lungs through a mouthpiece. In other cases, the nebulizer may be coupled to an inhalation mask.

Nebulizers operate by passing a stream of air or other suitable gas, such as medical oxygen, over or through a reservoir holding an aqueous solution of a drug for inhalation. In many cases, a stream of pressurized gas enters the nebulizer through a gas inlet and through a jet to produce a Venturi effect that draws a stream of the solution through a narrow passage or capillary from a pressure differential, whereby the liquid enters the jet and becomes atomized. Typically, a baffle is employed in the jet effluent that prevents large droplets from exiting the device, so that only aerosol micro-droplets of drug containing solution exit the device. An example of such a nebulizer is disclosed in U.S. Pat. No. 4,588,129. The aerosol is then inhaled by the patient. Typically, the aerosol production is continuous, so a vent is typically provided to ensure that the pressure differential created by the jet operates continuously and consistently.

The drug reservoir in nebulizers is usually a cone, cup, or bowl-shaped vessel into which a sterile aqueous solution of the drug is added. Accordingly, the orientation of the nebulizer is important, and the device must be kept approximately in an orientation such that the drug-containing solution stays in the reservoir where it can be aerosolized in the nebulizer. This restricts the range of motion available to the patient and nebulizer during use.

Typical drugs used with nebulizers are drugs for the treatment of asthma and obstructive pulmonary diseases, but other pulmonary and systematic medications may be administered by inhalation with nebulizers. For example, albuterol (called salbutamol in many countries), used for treating asthma and bronchospasm, may be administered as a nebulized solution. Another example is pentamidine, a drug used to treat Pneumocystis pneumonia (PCP).

Nebulizers are particularly useful for the administration of inhaled drugs to small children, elderly, unconscious, or disabled patients who cannot coordinate their breathing or take instruction on the use of coordinated inhalation devices, such as a metered dose inhaler. With a nebulizer, the dose of drug is administered to the patient over a period of several minutes, and possibly ten to twenty (or more) tidal or slow deep inhalations per minute, so breathing coordination is not required.

In the case of patients who cannot hold a mouthpiece in their mouth, an inhalation mask may be used with a nebulizer. This creates a complication in that the orientation of the mask and the nebulizer apparatus is important, to maintain the drug-containing solution in the reservoir for nebulization. Most nebulizer masks currently on the market have relatively inflexible connectors from the mask to the nebulizer apparatus and typically have a corrugated tube with a fixed 90° elbow for connection to a nebulizer. This requires that the patient inhale the mist while sitting straight in order to keep the nebulizer approximately vertical to avoid spilling the drug solution in the nebulizer or having the solution flow away from the capillary that carries the drug to the air-jet of the Venturi.

SUMMARY OF THE INVENTION

In one aspect, there is provided a swivel adapter for use as an airway with a nebulizer for inhaled drugs, wherein the adapter has a 90° elbow section, including a flanged joint comprising a frusto-spherical male section embedded in a matching frusto-spherical female section, that is pivotally flexible and can swivel over a broad range of angles and maintain a rigid airway at any angle. This apparatus with a ball-and-socket type of joint fits on the aerosol outlet of a nebulizer and allows a mouthpiece or mask to be adapted to the patient's most comfortable position while keeping the nebulizer in a roughly vertical orientation. In an embodiment, a method of using a nebulizer with a tube with a swivel adapter and a 90° elbow section, including a flanged joint, is provided. The adapter is used to convey an aerosolized drug from a nebulizer to the respiratory tract of a patient via inhalation through the nose and/or mouth.

DETAILED DESCRIPTION

In an embodiment, this invention discloses an adapter tube for use with a nebulizer for an inhalable drug, wherein the adapter comprises a pivotally flexible swivel joint that can swivel in any direction up to about 45° from its normal position, by use of a ball-and-socket type of flanged connector that provides a rigid airway regardless of the angle of use. The inhalable drug may be any drug intended for administration to the respiratory tract or lungs of a patient in need of such drug.

As used in the discussion herein, the term "proximal" means the section, orientation, or part closest to the face of a patient. The term "distal" means the section, orientation, or part closest to the nebulizer. Thus, the aerosol effluent from a nebulizer flows from the distal to the proximal end of the adapter in use.

Figure 4:
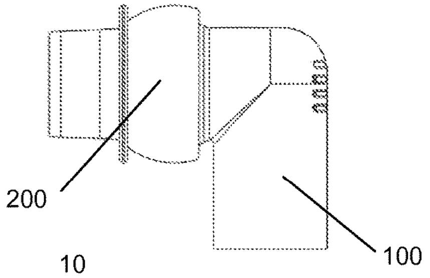
FIG. 4 is a side elevation view of the inventive device.
Figure 5:
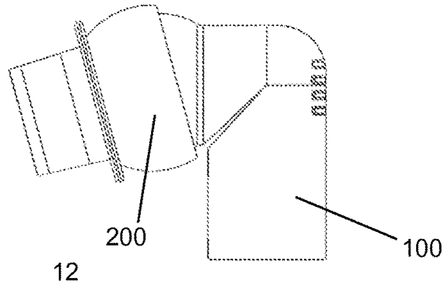
FIG. 5 is a side elevation view with the linear tubular member flexed approximately 15°.
Figure 6:
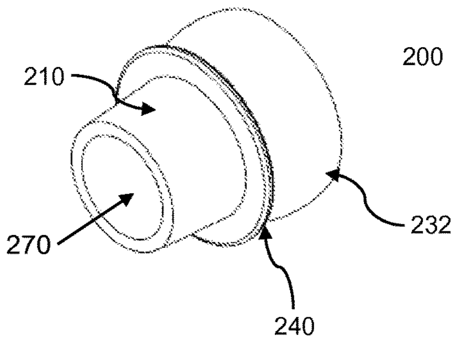
FIG. 6 is a perspective view of the linear tubular member.

Referring to the drawings, the embodiment in FIGS. 3-10 provides an adapter tube 10 defining a rigid aerosol-conducting airway with a swivel joint comprising of a ball-and-socket type of joint with a high degree of pivotal flexibility. The adapter 10 has two major components, 90° elbow tube member 100, and linear tubular member 200, arranged so that the proximal end of 100 comprises a frusto-spherical shape 130, also termed a nipple, on the outer surface of the proximal end. Member 200 comprises a cup-like frusto-spherical shape 230 on the inner surface of its distal end. Surface 130 nests inside of surface 230, as shown in cross-section in FIG. 10. When the nipple is nested in the cup, member 200 can pivot in any direction with respect to member 100 within a universal and continuous range of motion of approximately 45° in any direction. Member 200 is illustrated bent approximately 15° as 12 in FIG. 5. Member 200 is illustrated in FIG. 4 with no bend; that is, the angle measured through and along the axis of the pivotally flexible joint is 0° in FIG. 4. At all angles, the adapter 10 provides a rigid airway around the ball-and-socket pivotally flexible joint. In some embodiments, there is a tight seal preventing air leakage around the ball-and-socket pivotally flexible joint regardless of the pivot angle, preventing loss of drug through the joint.

As shown in the embodiment of FIGS. 3-10, the distal end of member 100 comprises tubular section 110 that defines airway 150 which is connected to the outlet of a nebulizer. The section 110 is intended to make a female connection to a nebulizer male aerosol outlet. Member 100 has 90° elbow bend portion 160 proximal to tube 110. Frusto-spherical section 130 is proximally oriented with respect to section 160.

As shown in the embodiment of FIGS. 3-10, the proximal end 210 of member 200 defines an airway 270 that is connected to a mouthpiece or inhalation mask as a male connector that conveys an aerosolized drug into the mouth or nose of a patient. The distal end of member 200 comprises a bulbous section 232 with an interior surface 230 defining a frusto-spherical shape, within which surface 130 nests in the complete adapter 10. Member 200 may optionally employ an annular flange 240 to assist in proper positioning of the mouthpiece or inhalation mask. Flange 240 may also be useful in providing a manual grip on the adapter when inserting the adapter 10 on to a nebulizer or into a mouthpiece or inhalation mask.

Thus, in an embodiment, an adapter tube is provided defining an aerosol-conducting airway with a pivotally flexible swivel joint for the use with an inhalation mask or mouthpiece with a nebulizer for the administration of an inhaled drug to the respiratory tract of a patient, where the adapter tube includes a first 90° elbow tube member with an interior surface and outer surface, a distal leg and a proximal leg, wherein the distal leg and proximal leg are oriented at a 90° angle, and the distal leg comprises a cylindrical section adapted for fitting on to a nebulizer, and the proximal leg comprises a frusto-spherical convex outer surface; a second linear tubular member with an interior surface and outer surface, a distal section and a proximal section, wherein the distal section comprises a concave frusto-spherical flange on the interior surface of the distal section of said tubular member, and wherein the proximal section is adapted for fitting into an inhalation mask or mouthpiece; and the proximal outer-surface frusto-spherical section of the 90° elbow member fits inside the distal frusto-spherical flange of the linear tubular member to form a pivotally-flexible swivel joint providing a rigid pivotally flexible airway for conveying an aerosolized drug to the respiratory tract of the patient.

In an embodiment, the orientation of the pivotally-flexible ball-and-socket connection may be reversed; that is, the female frusto-spherical section (the "socket" component) may be on the elbow member corresponding to member 200, and the male frusto-spherical section (the nipple or "ball" component) may be on the tubular section corresponding to member 100.

The adapter as disclosed herein may optionally include vent openings, illustrated in the drawings as 140, that may be necessary to equalize the pressure within the device, so that the nebulizer jet creates the desired pressure differential (Venturi effect) to draw the drug-containing solution into the jet where it is nebulized. In the case of continuous nebulization, vents are required to equalize the pressure and carry the aerosol away from the patient. In other embodiments, for example with a breath-actuated nebulizer, no vent holes will be provided. In some embodiments, including that shown in FIGS. 3-10, the ball-and-socket swivel joint makes a tight seal, which may be important in some applications, for example with the use of a breath-actuated nebulizer.

Thus, the adapter 10 can be used with a conventional continuous nebulizer, or with a breath-actuated nebulizer. In a conventional continuous nebulizer, a steady flow of aerosol is produced. In such devices, the mouthpiece is typically vented, keeping the pressure balanced in the nebulizer, but permitting aerosolized drug to escape from the device. With many drugs (for asthma therapy, for example) the escape and wasting of drug aerosol is not a problem, particularly if the drug is inexpensive and non-sensitizing.

Other vent configurations are also possible besides a type of configuration depicted as 140 in the Figures. For example, vent openings can be elsewhere on the adapter. In an embodiment, there may be vent openings within the ball-and-socket pivotally flexible joint.

Figure 7:
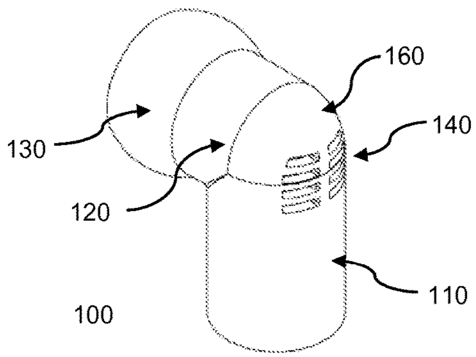
FIG. 7 is a perspective view of the 90° elbow tube member.
Figure 8:
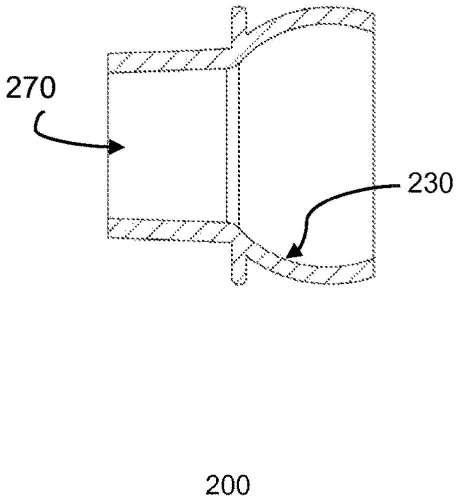
FIG. 8 is a cross-sectional view of the linear tubular member.
Figure 9:
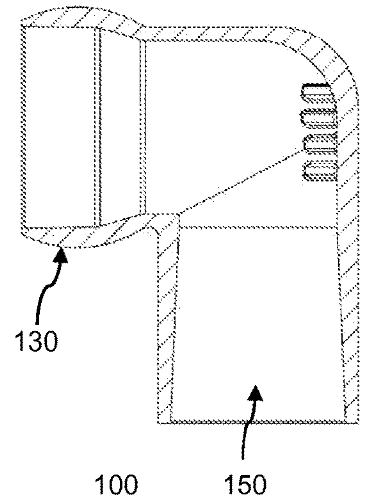
FIG. 9 is a cross-sectional view of the 90° elbow tube member.
Figure 10:
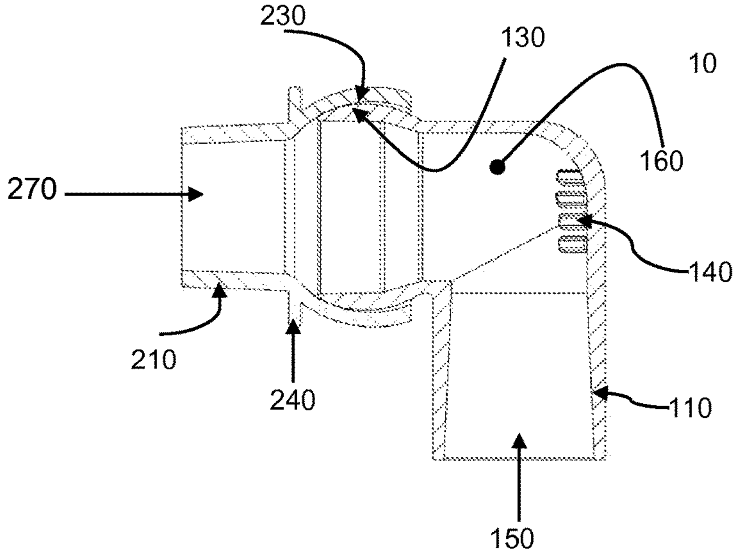
FIG. 10 is a cross-sectional view of the inventive device, showing the 90° elbow tube member nested into the flange of the linear tubular member.
Figure 11:
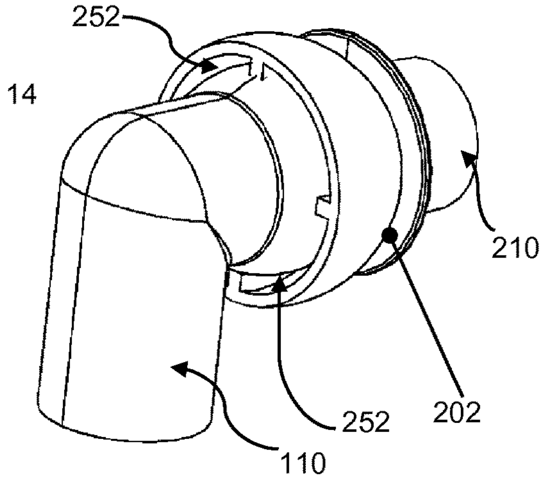
FIG. 11 is a perspective view of an alternative embodiment of this invention with a ribbed seat in the joint providing venting.
Figure 12:
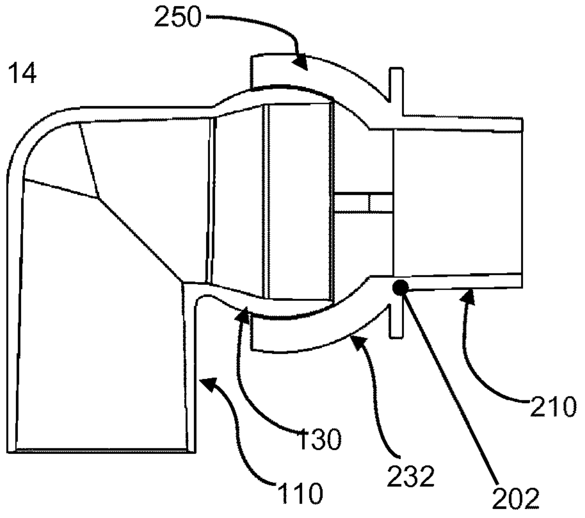
FIG. 12 is a cross-section of the embodiment with a ribbed seat in the joint providing venting.
Figure 13:
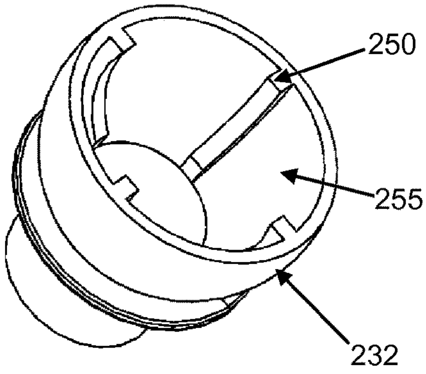
FIG. 13 is a perspective of the linear tubular member with a ribbed seat in the joint providing venting.
Figure 14:
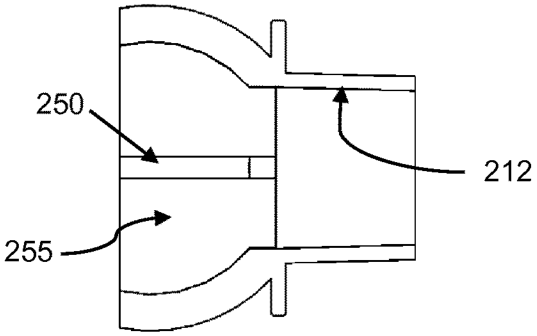
FIG. 14 is a cross section of the linear tubular member with a ribbed seat in the joint providing venting.
Figure 15:
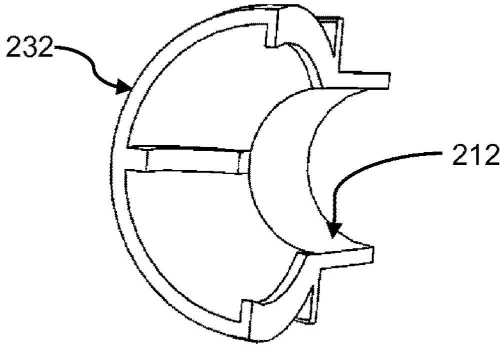
FIG. 15 is a cutaway view of the linear tubular member with a ribbed seat in the joint providing venting.

An alternative embodiment 14 of the inventive adapter is shown in FIGS. 11-15, providing a ribbed seat in the ball-and-socket joint that provides venting in the adapter. As shown in FIGS. 11-15, a 90° elbow member 100 with a convex frusto-spherical nipple shape 130 on the proximal end similar to FIGS. 7 and 9 is employed, but without vent openings 140. The linear tubular member 202 in this embodiment has a frusto-spherical portion 232 at the distal end, but the cup-like portion of member 202 has ribs 250 in the interior surface in which nipple 130 is seated. This is shown in perspective in FIG. 11 and in cross section in FIG. 12. The interior surface 255 of the cup-like distal portion of member 202 creates vent openings 252 in the assembled embodiment 14. The vents 252 provide fluid communication between 212, the proximal interior portion of member 202, and the exterior of the adapter 14. FIG. 13 is a perspective view of member 202, showing the ribs extending the full length of interior surface 255. FIGS. 14 and 15 show the ribs extending the full length of interior surface 255 to cylindrical interior surface 212. As is illustrated in FIG. 12, surface 130 when seated does not extend fully into the cup-like portion of 202, so the vent openings defined by ribs 250 are not blocked by surface 130.

In an alternative, the opposite arrangement to FIGS. 11-15 may be employed (not shown), with the nipple on the linear tubular member and the cup-like portion on the 90° elbow member.

In recent years, breath-actuated nebulizers have become available, for example the "AeroEclipse®" available in the United States from Monaghan Medical Corporation. These devices have a mechanism that prevents aerosolization within the device except when the patient is actually inhaling. There is no free vent allowing un-inhaled drug to escape during exhalation. Such devices are particularly useful where either the cost of the drug is very high or when the drug is sensitizing to caregivers (e.g. antibiotics), making wastage undesirable. Breath-actuated nebulizers are also useful where the dose of inhaled drug is critical, since without the wastage of a conventional nebulizer, the caregiver can be more certain of the amount of drug actually inhaled by the patient.

Also disclosed herein is a method of using a nebulizer with an adapter interposed between the nebulizer body and a mouthpiece or inhalation mask, allowing a degree of flexibility in the positioning of the device relative to the patient using the device. In an embodiment, this may provide a more comfortable position for the patient, since a nebulizer (as noted above), must typically be maintained in an approximately vertical orientation so that the drug-containing solution is properly oriented in the reservoir for nebulization. In most cases, nebulizers are cylindrical in shape and must be kept in an approximately vertical orientation in use. Thus, the pivotally flexible adapter may provide a more comfortable position for a patient. In another embodiment, the patient may be incompetent (unable to take instructions even to sit up) or unconscious. In such cases, in which an inhalation mask would normally be used, the inventive adapter gives caretakers enhanced flexibility in orienting the patient and/or the nebulizer for effective administration of the drug.

Figure 1A:
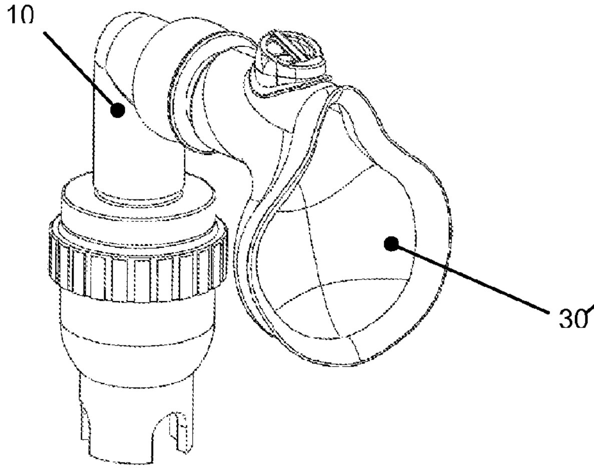
FIGS. 1A and 1B are perspective views of a complete nebulizer and inhalation mask apparatus including the inventive swivel adapter.
Figure 1B:
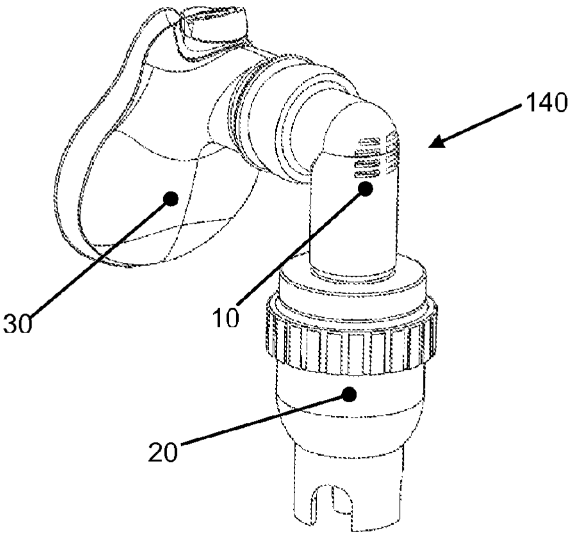

The adapter with an inhalation mask is shown in FIG. 1, which illustrates a complete kit of nebulizer 20, adapter 10 according to this disclosure, and an inhalation mask 30 that fits over the nose and mouth of a patient. Two views of the mask embodiment are shown in FIG. 1. FIG. 1A shows a view of the opening of the mask, that covers the nose and mouth of the patient. FIG. 1B shows the back view of the same apparatus as shown in FIG. 1A. Also shown in FIG. 1B are optional vents 140.

Figure 2A:
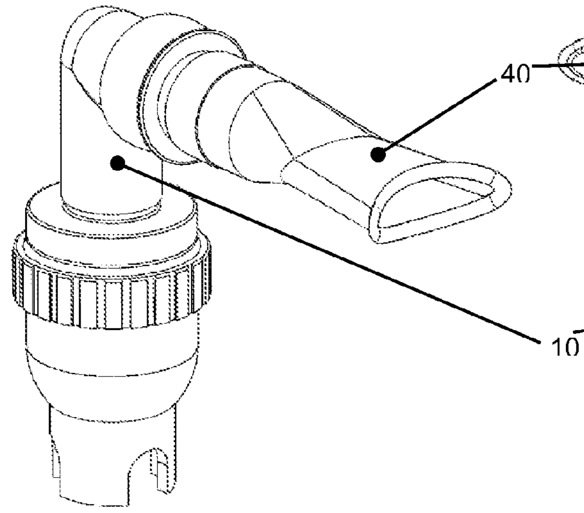
FIGS. 2A and 2B are perspective views of a complete nebulizer and mouthpiece apparatus including the inventive swivel adapter.
Figure 2B:
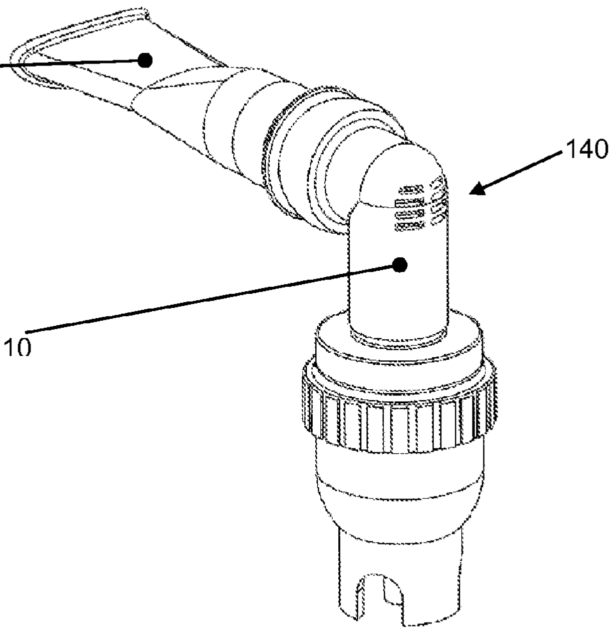
Figure 3A:
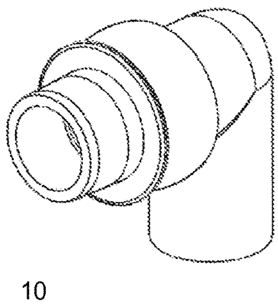
FIGS. 3A and 3B are perspective views of the inventive device.
Figure 3B:
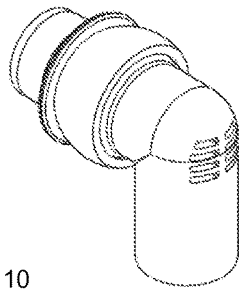

As shown in FIGS. 2A and 2B, the adapter 10 may be used with a mouthpiece 40 connected to tubular portion 210 (not marked). Such mouthpieces are well known in the art of using nebulizers, and simply convey the aerosol to the mouth of a patient for inhalation into the respiratory tract. The use of a mouthpiece is less expensive and easier for a caregiver if the patient is competent to take instructions to inhale through the mouth with the mouthpiece inserted between the closed lips and teeth.

The invention claimed is:

1. A kit, comprising:

an inhalation mask or mouthpiece;

a nebulizer that stores an inhalable drug and creates atomized suspension of the inhalable drug through a Venturi effect; and an adapter tube for joining the inhalation mask or mouthpiece with the nebulizer, such that the atomized suspension of the inhalable drug can be administered from the nebulizer to the respiratory tract of a patient through the inhalation mask or mouthpiece and the adapter, said adapter tube comprising:

a first member comprising an interior surface, an outer surface, a distal leg and a proximal leg, said first member being a 90° elbow tube, wherein the distal leg and the proximal leg are oriented at a 90° angle, the distal leg comprises a cylindrical section adapted for fitting onto the nebulizer, and the proximal leg comprises a proximal convex frusto-spherical outer surface section; and a second member comprising an interior surface, an outer surface, a distal section and a proximal section, said second member being linear tubular, wherein the distal section comprises a distal concave frusto-spherical portion, and wherein the proximal section is adapted for fitting into the inhalation mask or mouthpiece;

wherein the proximal convex frusto-spherical outer surface section of the first member fits inside the distal concave frusto-spherical portion of the second member to form a pivotally-flexible swivel joint providing a rigid pivotally flexible airway for conveying an aerosolized drug to the respiratory tract of the patient, wherein the distal concave frusto-spherical portion of the second member comprises at least three ribs provided on the interior surface of the second member, wherein the ribs are linear in the proximal-distal direction, wherein the proximal convex frusto-spherical outer surface section of the first member fits inside the ribs of the distal concave frusto-spherical portion of the second member to form the pivotally-flexible swivel joint, and wherein said ribs define vent openings in fluid communication with the proximal section of the second member and the exterior of the adapter tube, or wherein the proximal concave frusto-spherical portion of the first member comprises at least three ribs provided on the interior surface of the first member, wherein the ribs are linear in the proximal-distal direction, wherein the distal convex frusto-spherical outer surface section of the second member fits inside the ribs of the proximal concave frusto-spherical portion of the first member to form the pivotally-flexible swivel joint, and wherein said ribs define vent openings in fluid communication with the distal leg of the first member and the exterior of the adapter tube.

2. The kit of claim 1, wherein the second member further comprises an annular flange interposed between the distal section of the second member and the proximal section of the second member.

3. The kit of claim 1, wherein the pivotally-flexible swivel joint provides an airtight seal, with essentially no air leakage at the site of the joint.

4. The kit of claim 1, wherein the first member further comprises air vents.

5. A kit, comprising:

an inhalation mask or mouthpiece;

a nebulizer that stores an inhalable drug and creates atomized suspension of the inhalable drug through a Venturi effect; and an adapter tube for joining the inhalation mask or mouthpiece with the nebulizer, such that the atomized suspension of the inhalable drug can be administered from the nebulizer to the respiratory tract of a patient through the inhalation mask or mouthpiece and the adapter, said adapter tube comprising:

a first member comprising an interior surface, an outer surface, a distal leg and a proximal leg, said first member being a 90° elbow tube, wherein the distal leg and the proximal leg are oriented at a 90° angle, the distal leg comprises a cylindrical section adapted for fitting onto the nebulizer, and the proximal leg comprises a proximal concave frusto-spherical portion on the interior surface; and a second member comprising an interior surface, an outer surface, a distal section and a proximal section, said second member being linear tubular, wherein the distal section of said second member comprises a distal convex frusto-spherical outer surface section, and wherein the proximal section is adapted for fitting into the inhalation mask or mouthpiece;

wherein the distal convex frusto-spherical outer surface section of the second member fits inside the proximal concave frusto-spherical portion of the first member to form a pivotally flexible swivel joint providing a rigid pivotally flexible airway for conveying an aerosolized drug to the respiratory tract of the patient, wherein the distal concave frusto-spherical portion of the second member comprises at least three ribs provided on the interior surface of the second member, wherein the ribs are linear in the proximal-distal direction, wherein the proximal convex frusto-spherical outer surface section of the first member fits inside the ribs of the distal concave frusto-spherical portion of the second member to form the pivotally-flexible swivel joint, and wherein said ribs define vent openings in fluid communication with the proximal section of the second member and the exterior of the adapter tube, or wherein the proximal concave frusto-spherical portion of the first member comprises at least three ribs provided on the interior surface of the first member, wherein the ribs are linear in the proximal-distal direction, wherein the distal convex frusto-spherical outer surface section of the second member fits inside the ribs of the proximal concave frusto-spherical portion of the first member to form the pivotally-flexible swivel joint, and wherein said ribs define vent openings in fluid communication with the distal leg of the first member and the exterior of the adapter tube.

6. The kit of claim 1, wherein the nebulizer comprises a breath actuated nebulizer.

7. The kit of claim 5, wherein the second member further comprises an annular flange interposed between the distal section of the second member and the proximal section of the second member.

8. The kit of claim 5, wherein the pivotally-flexible swivel joint provides an airtight seal, with essentially no air leakage at the site of the joint.

9. The kit of claim 5, wherein the first member further comprises air vents.

10. The kit of claim 5, wherein the nebulizer comprises a breath actuated nebulizer.

11. A medical device, comprising:

an inhalation mask or mouthpiece;

a nebulizer that stores an inhalable drug and creates atomized suspension of the inhalable drug through a Venturi effect; and an adapter tube that joins the inhalation mask or mouthpiece with the nebulizer, such that the atomized suspension of the inhalable drug can be administered from the nebulizer to the respiratory tract of a patient through the inhalation mask or mouthpiece and the adapter, said adapter tube comprising:

a first member comprising an interior surface, an outer surface, a distal leg and a proximal leg, said first member being a 90° elbow tube, wherein the distal leg and the proximal leg are oriented at a 90° angle, the distal leg comprises a cylindrical section adapted for fitting onto the nebulizer, and the proximal leg comprises a proximal convex frusto-spherical outer surface section; and a second member comprising an interior surface, an outer surface, a distal section and a proximal section, said second member being linear tubular, wherein the distal section comprises a distal concave frusto-spherical portion, and wherein the proximal section is adapted for fitting into the inhalation mask or mouthpiece;

wherein the proximal convex frusto-spherical outer surface section of the first member fits inside the distal concave frusto-spherical portion of the second member to form a pivotally-flexible swivel joint providing a rigid pivotally flexible airway for conveying an aerosolized drug to the respiratory tract of the patient, wherein the distal concave frusto-spherical portion of the second member comprises at least three ribs provided on the interior surface of the second member, wherein the ribs are linear in the proximal-distal direction, wherein the proximal convex frusto-spherical outer surface section of the first member fits inside the ribs of the distal concave frusto-spherical portion of the second member to form the pivotally-flexible swivel joint, and wherein said ribs define vent openings in fluid communication with the proximal section of the second member and the exterior of the adapter tube, or wherein the proximal concave frusto-spherical portion of the first member comprises at least three ribs provided on the interior surface of the first member, wherein the ribs are linear in the proximal-distal direction, wherein the distal convex frusto-spherical outer surface section of the second member fits inside the ribs of the proximal concave frusto-spherical portion of the first member to form the pivotally-flexible swivel joint, and wherein said ribs define vent openings in fluid communication with the distal leg of the first member and the exterior of the adapter tube.

12. The medical device of claim 11, wherein the second member further comprises an annular flange interposed between the distal section of the second member and the proximal section of the second member.

13. The medical device of claim 11, wherein the pivotally-flexible swivel joint provides an airtight seal, with essentially no air leakage at the site of the joint.

14. The medical device of claim 11, wherein the first member further comprises air vents.

15. The medical device of claim 11, wherein the nebulizer comprises a breath actuated nebulizer.

16. A medical device, comprising:

an inhalation mask or mouthpiece;

a nebulizer that stores an inhalable drug and creates atomized suspension of the inhalable drug through a Venturi effect; and an adapter tube that joins the inhalation mask or mouthpiece with the nebulizer, such that the atomized suspension of the inhalable drug can be administered from the nebulizer to the respiratory tract of a patient through the inhalation mask or mouthpiece and the adapter, said adapter tube comprising:

a first member comprising an interior surface, an outer surface, a distal leg and a proximal leg, said first member being a 90° elbow tube, wherein the distal leg and the proximal leg are oriented at a 90° angle, the distal leg comprises a cylindrical section adapted for fitting onto the nebulizer, and the proximal leg comprises a proximal concave frusto-spherical portion on the interior surface; and a second member comprising an interior surface, an outer surface, a distal section and a proximal section, said second member being linear tubular, wherein the distal section of said second member comprises a distal convex frusto-spherical outer surface section, and wherein the proximal section is adapted for fitting into the inhalation mask or mouthpiece;

wherein the distal convex frusto-spherical outer surface section of the second member fits inside the proximal concave frusto-spherical portion of the first member to form a pivotally flexible swivel joint providing a rigid pivotally flexible airway for conveying an aerosolized drug to the respiratory tract of the patient, wherein the distal concave frusto-spherical portion of the second member comprises at least three ribs provided on the interior surface of the second member, wherein the ribs are linear in the proximal-distal direction, wherein the proximal convex frusto-spherical outer surface section of the first member fits inside the ribs of the distal concave frusto-spherical portion of the second member to form the pivotally-flexible swivel joint, and wherein said ribs define vent openings in fluid communication with the proximal section of the second member and the exterior of the adapter tube, or wherein the proximal concave frusto-spherical portion of the first member comprises at least three ribs provided on the interior surface of the first member, wherein the ribs are linear in the proximal-distal direction, wherein the distal convex frusto-spherical outer surface section of the second member fits inside the ribs of the proximal concave frusto-spherical portion of the first member to form the pivotally-flexible swivel joint, and wherein said ribs define vent openings in fluid communication with the distal leg of the first member and the exterior of the adapter tube.

17. The medical device of claim 16, wherein the second member further comprises an annular flange interposed between the distal section of the second member and the proximal section of the second member.

18. The medical device of claim 16, wherein the pivotally-flexible swivel joint provides an airtight seal, with essentially no air leakage at the site of the joint.

19. The medical device of claim 16, wherein the first member further comprises air vents.

20. The medical device of claim 16, wherein the nebulizer comprises a breath actuated nebulizer.

* * * * *